US012605393B2

(12) United States Patent
Björkholm et al.

(10) Patent No.: US 12,605,393 B2
(45) Date of Patent: Apr. 21, 2026

(54) COMPOSITIONS FOR ORAL OR NASAL USE

(71) Applicant: LIW INNOVATION AB, Hökerum (SE)

(72) Inventors: Lars Björkholm, Borås (SE); Johan Björkholm, Ulricehamn (SE)

(73) Assignee: LIW INNOVATION AB, Hökerum (SE)

( * ) Notice: Subject to any disclaimer, the term of this patent is extended or adjusted under 35 U.S.C. 154(b) by 580 days.

(21) Appl. No.: 17/922,623

(22) PCT Filed: May 7, 2021

(86) PCT No.: PCT/SE2021/050431
§ 371 (c)(1),
(2) Date: Nov. 1, 2022

(87) PCT Pub. No.: WO2021/225509
PCT Pub. Date: Nov. 11, 2021

(65) Prior Publication Data
US 2023/0165850 A1      Jun. 1, 2023

(30) Foreign Application Priority Data
May 7, 2020      (SE) .................................. 2050532-7

(51) Int. Cl.
| | |
|---|---|
| *A61K 9/16* | (2006.01) |
| *A61K 9/00* | (2006.01) |
| *A61K 31/00* | (2006.01) |
| *A61K 31/465* | (2006.01) |

(52) U.S. Cl.
CPC .......... *A61K 31/658* (2023.05); *A61K 9/0043* (2013.01); *A61K 9/0053* (2013.01); *A61K 9/1652* (2013.01); *A61K 9/1694* (2013.01); *A61K 31/465* (2013.01)

(58) Field of Classification Search
None
See application file for complete search history.

(56) References Cited

U.S. PATENT DOCUMENTS

| | | | |
|---|---|---|---|
| 2003/0073715 A1 | 4/2003 | El-Rashidy | |
| 2005/0075432 A1 | 4/2005 | Verrall | |
| 2005/0226823 A1 | 10/2005 | Krumme | |
| 2007/0269492 A1 * | 11/2007 | Steen ..................... | A61P 25/34 424/440 |
| 2013/0177646 A1 | 7/2013 | Hugerth | |
| 2013/0186418 A1 | 7/2013 | Gao | |
| 2017/0172995 A1 | 6/2017 | Repaka | |

FOREIGN PATENT DOCUMENTS

| | | | | |
|---|---|---|---|---|
| EP | 2405942 B1 * | 11/2017 | .......... | A61K 31/465 |
| WO | 0054777 A1 | 9/2000 | | |
| WO | WO-2005023227 A2 * | 3/2005 | ............. | A61P 25/28 |
| WO | 2005048980 A1 | 6/2005 | | |
| WO | 2007104574 A2 | 9/2007 | | |
| WO | 2010104464 A1 | 9/2010 | | |
| WO | 2010114445 A1 | 10/2010 | | |
| WO | 2013143891 A1 | 10/2013 | | |
| WO | WO-2018089863 A1 * | 5/2018 | ............. | A61K 31/05 |
| WO | 2019/219773 A1 | 11/2019 | | |
| WO | 2019224323 A1 | 11/2019 | | |

OTHER PUBLICATIONS

International Search Report from corresponding International Application No. PCT/SE2021/050431, mailed on Sep. 7, 2021, 6 pages.
Search Report from corresponding Swedish Application No. 2050532-7, mailed on Nov. 24, 2020, 4 pages.

* cited by examiner

*Primary Examiner* — Susan T Tran
(74) *Attorney, Agent, or Firm* — Tucker Ellis LLP

(57) ABSTRACT

The specification discloses compositions for use in the oral or nasal cavity comprising a biologically active agent, a matrix forming agent comprising alginate and suitable salts thereof, a filling agent and at least one antioxidant that is an effective complex binder. The compositions can further comprise additional excipients such as preservatives, taste or flavour enhancers, pH adjusters, plasticizers and sweeteners. The specification also discloses methods of producing the compositions.

21 Claims, No Drawings

COMPOSITIONS FOR ORAL OR NASAL USE

TECHNICAL FIELD

The present invention relates to compositions for use in the oral or nasal cavity comprising a biologically active agent, a matrix forming agent, comprising alginate and salts thereof, a complex binding antioxidant and a filling agent and method of producing the compositions.

BACKGROUND ART

Delivery of pharmaceutically active agents to oral and nasal cavity is generally a desirable administration route to obtain a fast or controlled therapeutic onset and to avoid the metabolic activities of the gastrointestinal system and of a first by-pass metabolism. Numerous solid dose forms such as lozenges, sublingual tablets, chewing gums, buccal patches or pouches have been developed to obtain compliant dose forms for patients depending on therapies through the oral cavity. Such solid dose forms typically include active agents, fillers, binders, lubricants and other ingredients supporting mucoadhesiveness, palatability, compliance and release of an active agent.

Suppliers and developers of smokeless tobacco and nicotine products have developed numerous products configured to deliver nicotine through the oral or nasal cavity. Tobacco products include for example chewing tobacco, moist smokeless tobacco, snus and dry snuff to be used orally or nasally. Non-tobacco products rely on pure nicotine extracted from tobacco or synthetic nicotine formulated with suitable additives to an oral or nasal dose form as exemplified. For the oral cavity non-tobacco dose forms can for example rely on a fibrous filler material and matrix forming agent acting as a binder. Nicotine (3-(1-methyl-2-pyrrolidinyl) pyridine is a volatile compound liable to degradation under the influence of heat, oxygen and light. For this reason, it is a technical challenge to find a suitable non-tobacco dose form as a product that counteracts degradation during its manufacturing and provides a suitable storage stability of nicotine while admitting a desirable release rate of nicotine in the oral cavity and yet is compliant to the user.

There are several disclosures of products suitable for delivery of active agents to the oral cavity such as WO2005048080; WO0054777; US200307315; WO 20100104464 that disclose a matrix forming agent and an antioxidant. Antioxidants. WO 2007104574; US2005226823; US2013186418 disclose various orally useful nicotine compositions that include an antioxidant, but do not disclose any matrix forming agent. WO2013143891 discloses an alginate based nicotine containing oral film without giving particular guidance to stabilizing nicotine. WO2019224323 discloses another alginate based oral film with antioxidants for delivering other agents than nicotine.

WO 2010/011445 discloses a plant fiber product for oral use suitable for delivery of active agents such as nicotine. The incorporation of alginate as matrix former provides the product with desirable release characteristics and a suitable stabilization of liable active agents. WO 2010/104464 discloses particles of alginate comprising active agent such as nicotine enclosed in pouches for use in the oral cavity. WO 2010/0104464 indicates that the alginate matrix may form an oxygen barrier and that no addition of an antioxidant may be required. However, certain very liable active agents would need further protection from degradation during long term storage, especially in systems with a high water content. For this reason, there is a need of additionally stabilized compositions relying on an alginate matrix, comprising antioxidants that are effective with alginate throughout a desirable pH range.

DESCRIPTION OF THE INVENTION

It is an object of the present invention to provide compositions suitable to deliver a biologically active agent to the oral or nasal cavity that admits stability of active agent throughout manufacturing and storage, while admitting a suitable release profile of said agent.

It is also an object of the present invention to provide compositions that supports a controlled release rate of active agent and a controlled, suitable duration of the release rate.

It is also an object of the present invention to provide compositions that promotes stabilization of active agents liable to degradation during storage to obtain stable products with long shelf life also in compositions with relatively high water content.

It is also an object of the present invention to provide compositions with high compliance with the mucosa of the oral nasal cavity in order to avoid local irritation and side-effects from repeated or long term exposure.

It is still another object of the invention to provide compositions suitable to deliver nicotine to the oral or nasal cavity and thereby satisfy the user expectations of compliance with comparable and conventional tobacco or nicotine products, or pharmaceutical products.

Another object of the invention is to by means of the manufacturing methods control nicotine bound to the matrix forming agent and unbound nicotine in order to provide an initially consumer satisfying nicotine dose together with a gradual nicotine release comparable to the release from conventional tobacco fibers, while exerting a suitable stabilizing of both bound and unbound nicotine throughout storage also high water content product compositions.

In a general aspect, the invention relates to a composition for use in the oral or nasal cavity having a pH of at least 6.5, comprising an active agent selected from nicotine and a cannabinoid, a matrix forming agent comprising alginate and suitable salts thereof, a filling agent and an antioxidant that is an effective complex binder at a pH of at least 6.5, comprising at least one ammonium citrate or a salt thereof.

In this general context, a matrix forming agent is capable of together with the filling agent provide a coherent, homogenous compositions that encompasses the biologically active agent and contribute to exert a stabilizing effect on liable such agents, while contributing to a controllable and desirable release profile of the active agent when in contact with the oral or nasal cavity. The stabilizing effects may or may not be caused by a synergy with the filling agent, for example between the matrix and fibers of a filling agent. In the inventive compositions, the affinity between the active agent and the matrix forming agent can be employed to adjust and control the release rate.

The matrix forming agent of the invention is used also to release nicotine in a controlled manner in the composition. For example, when the active agent is nicotine, the matrix forming agent can be selected so a controlled amount of nicotine is free, unbound nicotine and a controlled amount of nicotine is gradually and controllably released from the matrix forming agent. For example, by increasing the amount of matrix forming agent in the inventive compositions, more nicotine is bound and gradually released. The compositions of the invention can accordingly be developed to provide the user with a satisfying initial dose of nicotine administered to the oral or nasal cavity and be provided with a gradual release of nicotine from the composition during a predetermined time period. For a nicotine product the matrix forming agent can be used to meet different requests of user compliance.

The antioxidant comprises an ammonium citrate that is effective at a pH of 8 to 9 to for example complex bind metal ions in a composition with a high pH and contributes to stabilize the compositions throughout production and storage. The ammonium citrate is selected from ammonium citrate dibasic (ammonium hydrogen citrate), ammonium citrate tribasic (triammonium citrate) and ammonium citrate salts such as ammonium ferric citrate, most preferably, the ammonium citrate is ammonium citrate tribasic (triammonium citrate).

The antioxidant is present in an amount of less than 5% (w) in the inventive compositions, preferably in amount of 0.1 to 5% (wt) and most preferably from 0.5 to 1% (wt). The antioxidant can further comprise one of alkali and/or alkaline earth metal salts of ascorbate, calcium citrates, calcium lactates, calcium maleates, calcium tartrates, Ca-diNa-EDTA and calcium phosphates.

In one aspect, the compositions of the invention comprises less than 50% (wt) of the matrix forming agent, such as less than 40% (wt) or less than 30% (wt) and less than 20% (wt), or from 1 to 10% (wt), or from 0.5 to 5% (wt).

In another aspect, the compositions of the invention comprises more than 50% (wt) of the matrix forming agent, such as from 50 to 90% (wt), or from 50 to 70% (wt).

Also, in this general context, the filling agent will principally contribute to bulk and shape of the composition, for example in order to admit user compliance with different parts of the oral cavity and/or assist with conveniently manufacture, handle and administer the compositions. The filling agent may also in embodiments positively interact with the matrix forming agents to stabilize the agent(s) and induce desirable release properties.

Generally, suitable alginates for the invention are alginate salts of monovalent cations that are soluble in cold water and have a low viscosity. The skilled person is capable of selecting alginates with different viscosity, solubility and molecular weight in order to modify dissolution in water and also in the oral or nasal cavities. The alginate LFR 5/60 from Pronatal® is example of low viscosity alginate and Protanal® LF 10/60 (FMC BioPolymer) is an example of an alginate with higher viscosity. In order to obtain suitable dissolution and release profiles, it may be suitable to mix alginates with different viscosities. Alginate salts of divalent cations, for example Ca are generally less soluble and can be used in the inventive compositions in order to support specific release profiles an active agent, preferably in combination with one or more alginate salts of monovalent cations.

In one aspect, the compositions of the invention the matrix forming agent comprises at least 50% (weight) of alginate or salts thereof, for example 50 to 90% (wt) of alginate or salts thereof.

The compositions of the invention can comprise a matrix forming agent that further comprises at least one additional pharmaceutically acceptable gum or gel forming polysaccharide of food or pharmaceutical grade, preferably selected from beta-glucan comprising various grades of β (1-3) (1-4) glucan, xanthan, carrageenan, methyl cellulose, curdlan, pullulan, maltodextrin, guar gum, gum *arabicum* and similar polysaccharides, and when applicable suitable salts thereof.

The filling agent of the inventive compositions comprises a fiber material, which can be of natural or a synthetic source. The fiber is preferably derived from plants, algae or fungi and it can be natural or modified with bioprocesses or chemical methods. In preferred aspects, the fiber material is a plant fiber, more preferably the filling agent comprises natural or modified cellulose fibers and most preferably at least one microcrystalline cellulose. Many chemically modified celluloses are conceivable to be comprised in the filling agent of the compositions such as brands of methyl cellulose, carboxymethyl cellulose, hydroxyethyl cellulose and hydroxypropyl cellulose.

In various embodiments, the plant fibers comprised in the filling agent can be derived from one of tea, coffee, tobacco, cocoa, maize, bamboo, oat, barley, rye, sugar beets, herbs, buckwheat, potatoes, tomatoes, aubergins, cauliflower, apples, yerba mate or cellulose fibers various sources and the similar. The plant fibers can be natural or modified with various biological or chemicals methods. The tobacco fibers may be processed according to various conventional technologies for whiteness and/or reduction of nitrosamines.

Suitable microcrystalline celluloses (MCC) can be selected from AVICEL® grades PH-100, PH-102, PH-103, PH-105, PH-112, PH-113, PH-200, PH-300, PH-302, VIVA-CEL® grades 101, 102, 12, 20; EMOCEL® grades 50M and 90M, HiCel® grades, such as HiCel® 90M and the like, and mixtures thereof. For embodiments of the inventive compositions, wherein a water-soluble microcrystalline cellulose is desirable such as powdered compositions for use in the nasal cavity, suitable grades of colloid microcrystalline cellulose are the grade with Cas No. 51395-75-6, such as various brands of TABULOSER. A preferred such colloid gelling MCC has the trade name FEIYUN XW591.

In embodiments of the inventive compositions, the filling agent comprises a polyol, preferably a polyol selected from one or more mannitol, xylitol, sorbitol, maltitol and/or isomaltitol, lactitol and erythritol. Suitably, the inventive compositions comprise a filling agent that comprise a plant fiber material and 5 to 70% (wt) of a polyol. According to an example, the filling agent comprises mannitol and at least one microcrystalline cellulose. According to other examples of the invention such lozenges or tablets for use, the filling agent can exclusively be a polyol as defined.

In embodiments of the invention directed to powdered compositions for use in the nasal cavity, the filling agent can comprise a mucoadhesive agent selected from at least one of a cellulose derivative, a starch derivative and a polyvinylpyrrolidone, preferably the mucoadhesive agent is selected from at least one of sodium starch glycolate and crosslinked polyvinylpyrrolidone. In such embodiments the filling agent can comprise a guar gum or a starch. Suitable starches are corn starch, pregelatinized starch, hydroxypropyl starch and modified or unmodified starch.

In embodiments of the invention directed to powdered compositions for use in the nasal cavity, the composition comprises powder particles with a controlled average size (diameter) of such as from 0.01 to 2 mm, or 0.05 to 0.5 mm, or 0.02 to 0.2 mm, or 0.01 to 0.1 mm. For the compositions, the powder particle size is optimized with considerations to avoid aerosolization and to risk inadvert powder distribution to the lungs when particles approach <10 μm in size and to avoid insufficient compliance and distribution with large particles exceeding about a few millimeters in size.

Generally, the compositions according to the invention are useful for an active agent that can be a therapeutic or non-therapeutic substance not conventionally considered as a pharmaceutical, such as a naturopathic preparation, a stimulant or a nutraceutical. Examples of therapeutic biologically active substances that are suitable to be administered alone or in combinations by the inventive compositions include urinary incontinence agents; antihistamines, analgesics, anti-inflammatory agents, antiemetics, anti-epileptics, vasodilators, antitussive agents and expectorants, anti-spasmodics, hormones, diuretics, anti-hypotensives, bronchodilators, anti-inflammatory steroids, antibiotics, sedatives, CNS-active substances, decongestants, laxatives and antacids. Generally, the compositions are useful as drug delivery dose forms for patients suffering from complications leading to incapacity of receiving conventional tables for swallowing such as unconsciousness, severe migraine, acute stroke or gastrointestinal obstructions. Examples of suitable non-therapeutic agents are caffeine, alcohol powder, ethanol, vitamin B12, vitamin C, vitamin E, Bioperin®, Coenzyme Q10, selenium, glutathione, alpha liponic acid, folic acid, ginseng, pollen extract, antioxidants, minerals, paracetamol, acetylsalicylic acid, Russian root and rose root, etc.

In one aspect, the biologically active agent is nicotine or a cannabinoids such as A9-tetrahydrocannabinol (THC) or cannabidiol (CBD), The term nicotine includes synthetic nicotine and nicotine extracts from tobacco plants such as the genus *Nicotiana* or other plant sources and includes nicotine or a nicotine derivative in any solid or liquid form such as, e.g., physical form like amorphous, crystalline, polymorphous etc. or chemical form like isomers and enantiomers etc. as well as any pharmaceutically acceptable salt, complex or solvate thereof. Nicotine forms herein include nicotine base, and/or salts of nicotine, such as nicotine hydrochloride, nicotine dihydrochloride, nicotine monotartrate, nicotine bitartrate, nicotine sulphate, nicotine zinc chloride (monohydrate) and nicotine salicylate.

Nicotine is typically present in a concentration from about 0.1% (wt) to about 5% w/w, such as, e.g., from about from about 0.1% (wt) to about 4% (wt), from about 0.1% to about 3% (wt), from about 0.1% (wt) to about 2% w/w, from about 0.1% (wt) to about 1% (wt), from about 0.1% (wt) to about 0.75% (wt), from about 0.2% (wt) to about 0.5% (wt) or from about 0.2% (wt) to about 0.4% (wt), calculated as free base. The nicotine or its salts used with the inventive compositions preferably is of high purity, such as 99.5% purity.

The compositions according to the invention further comprises at least one excipient selected from plasticizers, pH adjusters, preservatives, taste or flavour enhancers, colouring agents and sweeteners.

The plasticizer is selected from e.g., polyethylene glycols, propylene glycols, glycerol and sorbitol. A preferred plasticizer is sorbitol, optionally together with a part of glycerol.

The pH adjuster is capable of maintaining a pH of at least 6.5 in the compositions and is exemplified by carbonates including monocarbonate, bicarbonate and sesquicarbonate, and other alkali/alkaline metal salts of physiologically acceptable acids such as acetates, glycinates, gluconates, borates, glycerophosphates or weak organic acids such as citric acid, phosphates, metal hydroxides such as sodium hydroxide and potassium hydroxide, and mixtures thereof. Examples of suitable pH adjusters are sodium bicarbonate and sodium carbonate, and mixtures thereof. It is preferable that the pH is higher at production of the compositions, such as a pH of 8 to 9, but the pH adjuster shall be capable of keeping the pH>6.5 throughout storage and consumption.

A preservative can be selected from selected from approved agents in food and pharmaceutical industry such as sorbic acid, sorbates, benzoic acid lactic acid and physiologically acceptable salts. A preferred preservative is potassium sorbate.

Taste or flavor enhancers include ammonium chloride, essential oils including distillations, solvent extractions or cold expressions of chopped flowers, leaves, peel or pulped whole fruit comprising mixtures of alcohols, esters, aldehydes and lactones or essences including either diluted solutions of essential oils or mixtures of synthetic chemical blends to match the desired flavour from for examples bergamot, eucalyptus, orange, mandarin, citrus, lemon, peppermint, mint, menthol, liquorice, wintergreen, tobacco, coffee, vanilla, lime, apple, peach and mixtures thereof. Further examples include artificial and natural flavours of brews and liquors, e.g., cognac, whiskey, rom, gin, sherry, port, and wine, eucalyptus, liquorice, and menthol.

Coloring agents can be selected from dyes containing chemical groups which absorb light including dyes, such as indigo carmine, amaranth, erythrosine, carbon black, titanium dioxide and any mixtures thereof.

Sweeteners or texture improves can be sugar alcohols including mannitol, xylitol, sorbitol, maltitol and/or isomalt, natural sweeteners such as sugars which preferably not fermentable in the mouth, or artificial sweeteners such as e.g., aspartame, acesulfame K, saccharin, cyclamates, *Stevia* extracts and other similar agents.

In one aspect, the compositions comprise less than 50% of the matrix forming agent, are adapted to delivery to the nasal cavity and comprises less than 20% (wt) water, preferably 1 to 15% (wt) of water. The powder particles have a size range of 0.01 to 2 mm. In an embodiment of this aspect, the filler comprises a water soluble cellulose, preferably water soluble microcrystalline cellulose, more preferably a combination of water soluble and water insoluble microcrystalline cellulose.

In one aspect, the compositions comprise less than 50% of the matrix forming agent, are adapted to contact with a mucous membrane of the oral cavity and comprise at least 30% (wt) of water, preferably at least 40% (wt) of water. Preferably, the filling agent is selected from at least one of microcrystalline cellulose and plant fibers. Preferably, the compositions comprise 40 to 60% (wt) water. Such high water content compositions are especially useful as conventional snus products giving high user compliance by being easy to form as a dose or to use in pouches.

In another aspect, wherein the compositions comprise less than 50% of the matrix forming agent and are adapted to contact with a mucous membrane of the oral cavity, the compositions comprise less than 40% (wt) of water. The filling agent is also selected from at least one of microcrystalline cellulose and plant fibers, preferably the composition comprises 1 to 30% (wt) of water.

In another aspect, the compositions comprise more than 50% of the matrix forming agent and are configured as a film suitable for transmucosal delivery of active agent. The film compositions have a thickness of 0.01 to 7 mm, preferably 0.01 to 3 mm and optionally include a plasticizer. In an embodiment, these compositions comprise 0.05 to 20% (wt), preferably 5 to 10% (wt) of filling agent, preferably the filling agent is a microcrystalline cellulose and a plasticizer, preferably the plasticizer is selected from at least one of sorbitol and glycerol.

The components and the amount of the filling agent and the other named excipients may vary depending on the desired properties of the final product, for example to obtain attractiveness for oral or nasal use.

In one embodiment suitable for oral use, the composition comprises nicotine, alginate and suitable salts thereof as the matrix forming agent, a filling agent comprising microcrystalline cellulose, at least 40% (w) water, a pH adjuster, an antioxidant comprising an ammonium citrate and other excipients selected from one or more preservatives, taste/flavour enhancers and sweeteners.

In another embodiment suitable for oral use, the composition comprises nicotine, alginate and suitable salts thereof as the matrix forming agent, a filling agent comprising microcrystalline cellulose and optionally additional plant fibers, 40 to 60% (wt) water, a pH adjuster, an antioxidant comprising an ammonium citrate and other excipients selected from one or more preservatives, taste/flavour enhancers and sweeteners.

In another embodiment suitable for oral use, the composition comprises nicotine, a matrix forming agent comprising alginate and suitable salts thereof and one or more other additional pharmaceutically acceptable gums, a filling agent comprising microcrystalline cellulose, a polyol, preferably mannitol and optionally additional plant fibers, 40 to 60% (wt) water, a pH adjuster, an antioxidant comprising an ammonium citrate and other excipients selected from one or more preservatives, taste/flavour enhancers and sweeteners.

In another embodiment suitable for oral use, the composition comprises nicotine, 0.5 to 10% (wt) alginate and suitable salts thereof as the matrix forming agent, 40 to 90% (wt) of a filling agent comprising microcrystalline cellulose and optionally additional plant fibers, 40 to 60% (wt) water, sodium bicarbonate as a pH adjuster, 0.1 to 5% (wt) of an ammonium citrate as an antioxidant and other excipients selected from one or more preservatives, taste/flavour enhancers and sweeteners.

In another embodiment suitable for oral use, the composition comprises nicotine, less than 40% (wt) alginate and suitable salts thereof as the matrix forming agent, a filling agent comprising microcrystalline cellulose and optionally plant fibers, 40 to 60% (wt) water, sodium bicarbonate as a pH adjuster, an ammonium citrate as an antioxidant and other excipients selected from one or more preservatives, taste/flavour enhancers and sweeteners.

In still another embodiment, the composition comprises, 0.5 to 1.5% (wt) nicotine; 0.5 to 1% (wt) of antioxidant comprising an ammonium citrate, preferably triammonium citrate; 0.5 to 10% (wt) of a matrix forming agent; 40 to 50% of filling agent; 40 to 50% (wt) of water; and other excipients selected from one or more pH adjusters, preservatives, taste/flavour enhancers and sweeteners In embodiment of the invention suitable as a lozenge of tablets to be gradually dissolved in the oral cavity, the composition comprises nicotine; 1 to 30% (wt) water; 50 to 90% (wt) of a matrix forming agent, comprising alginate and optionally an additional matrix forming agent as defined; an antioxidant comprising an ammonium citrate; and 1 to 40% (wt) of a filling agent.

In one embodiment suitable for nasal use, the composition comprises nicotine, alginate and suitable salts thereof as the matrix forming agent, a filling agent comprising of an at least partially water soluble cellulose, less than 20% (wt) water, a pH adjuster, an antioxidant comprising an ammonium citrate and other excipients selected from one or more preservatives, taste/flavour enhancers and sweeteners.

In one embodiment suitable for nasal use, the composition is a powder with particles of size of less that about 2 mm, and comprising nicotine, alginate and suitable salts thereof as the matrix forming agent, a filling agent comprising an at least partially water soluble cellulose, less than 20% (wt) water, a pH adjuster, a chelate forming antioxidant and other excipients selected from one or more preservatives, taste/flavour enhancers and sweeteners.

In another embodiment suitable for nasal use, the composition is a powder with particles of size in the range of 0.01 to 2 mm comprising nicotine, alginate and suitable salts thereof as the matrix forming agent, a filling agent comprising an at least partially water soluble cellulose, 1 to 15% (wt) water, sodium bicarbonate as a pH adjuster, a chelate forming antioxidant, preferably an ammonium citrate as an antioxidant and other excipients selected from one or more preservatives, taste/flavour enhancers and sweeteners.

These and other embodiments will be more fully exemplified in the following detailed description.

In another general aspect, the present invention is directed to methods of producing the compositions for use in the oral and nasal cavity. The methods comprise dry mixing the filling agent and at least one of the matrix forming agent, a an antioxidant and optionally taste or flavour enhancers; mixing the dry mixture with a first aqueous solution comprising a pH adjuster; adding a second aqueous solution comprising at least one of a preservative, a taste or flavour enhancer and a sweetener; adding a third aqueous solution comprising nicotine and finally mixing all added components to a mixture with a suitable amount of water, such as at least 30% water (wt).

In one embodiment of the method, the filling agent in the first step is dry mixed with the matrix forming agent, the antioxidant and optionally taste or flavour enhancers.

In one embodiment of the method, the filling agent in the first step is dry mixed with the antioxidant and optionally taste or flavour enhancers, and the third aqueous solution comprises the matrix forming agent nicotine.

The method can in one alternative be configured to produce a powder composition for nasal by use of one or more of further processing steps of the resulting mixture, comprising drying, for example spray drying, to a powder of a particle size of less than 1 mm with less than 20% water (wt), such as 1 to 15% (wt) of water.

The method can in another alternative be configured to produce a composition for use in the oral cavity by one or more further processing steps of the resulting mixture with at least one process of filling in pouches, tablet or lozenge forming, extrusion, punching, casting, moulding, injection moulding, kneading, spinning, film, dilution to a sprayable dose form, forming and admixing with chewing gum base.

DETAILED AND EXEMPLIFYING DESCRIPTION OF THE INVENTION

As used herein in both general and exemplifying contexts, weight percent (wt) % means percent weight of the total composition.

Table 1 below further illustrates examples of oral or nasal compositions including suitable excipients.

TABLE 1

| Ingredient | Use | Amount (wt %) |
| --- | --- | --- |
| Water | Humidification | 2-70% |
| Sodium Chloride | Taste | <15% |
| Microcrystalline cellulose | Filling agent | 5-95% |
| Sodium bicarbonate/carbonate | pH adjuster | <2% |
| Sodium alginate | Matrix forming agent | <5% |
| Ammonium chloride | Flavour | <2% |
| Potassium sorbate | Preservative | <0.2% |
| Xylitol | Sweetener | <5% |
| Acesulfame K/Stevia | Sweetener | <0.5% |
| Menthol/Spearmint/Lemon/Others | Flavour | <8% |
| tri-Ammonium citrate, CAS No. | Antioxidant | <5% |

TABLE 1-continued

| Ingredient | Use | Amount (wt %) |
|---|---|---|
| 3458-72-8. Nicotine | Active agent | <20% |

A specific example of a composition product made with the outlined methods is demonstrated in Table 2

TABLE 2

| Ingredient | Use | Amount (wt %) |
|---|---|---|
| Water | Humidification | 45.93 |
| Microcrystalline cellulose | Filling agent | 42.10 |
| Sodium Chloride | Taste | 5.22 |
| Flavour | Smell and taste | 1.86 |
| Xylitol | Sweetener | 1.74 |
| Nicotine | Active agent | 0.89 |
| Sodium alginate from Carl Roth GmbH Karlsruhe, Germany | Matrix forming agent | 0.70 |
| tri-Ammonium citrate, CAS No. 3458-72-8 | Antioxidant | 0.70 |
| Ammonium chloride | Taste | 0.35 |
| Sodium bicarbonate | pH adjuster | 0.26 |
| Potassium sorbate | Preservative | 0.2 |
| Acesulfame K | Sweetener | 0.07 |

Example 1

A composition in accordance with Table 2 without flavor with about 1% nicotine, having a pH of 8.5, suitable to be packaged in pouches as a snus type of product for use in the oral cavity was tested for stability of nicotine. Samples of 80 g of the composition of Table 2 and a commercial snus product based on tobacco were compared during 9 weeks at 40° C. and 75% relative humidity (comparable to 10 months at 25° C. see Table 3. For the compositions demonstrated in Table 3 equal amounts of different chelate forming antioxidants and a non-complex forming antioxidant were compared with the commercial product.

TABLE 3

| | Composition of Table 2 with ammonium citrate | Composition of Table 2 with calcium ascorbate | Composition of Table 2 with BHT | Commercial product |
|---|---|---|---|---|
| Water content % (wt) | 41.2 | 42.3 | 43.8 | 41.5 |
| Initial pH | 8.6 | 7.9 | 8.8 | 8.5 |
| pH after 9 weeks | 8.3 | 7.9 | 8.1 | 8.2 |
| Initial amount nicotine (mg) | 1 | 1.5 | 1.4 | 1.0 |
| Amount nicotine after 9 weeks (mg) | 0.85 | 0.99 | 0.58 | 0.76 |
| % loss of nicotine | 15% | 34% | 59% | 24% |

Table 3 demonstrates that the sodium alginate and an antioxidant of the inventive compositions results in a significant increase in nicotine stability This result indicates that a matrix forming agent comprising sodium alginate according to the inventive compositions has a comparable capacity of preserving nicotine as the natural tobacco fibers. A positive effect of ammonium citrate compared to calcium ascorbate can also been seen in this example. The negative effect of the non-complex forming antioxidant BHT (butyl-hydroxytoluene) can also be seen in Table 3. In conclusion, the combination of a matrix forming agent comprising an alginate salt and a complex binding antioxidant provides an effective long term stability of nicotine.

Example 2

The product with about 1% (wt) nicotine was made in accordance with Table 2 with the two embodied methods generally outlined above. In Process 1, sodium alginate is dry mixed with the MCC filling agent in a first step and a solution of nicotine is added in a third step. The product from Process 1 comprises 0.7% (wt) of sodium alginate. In Process 2, sodium alginate is added in a solution comprising nicotine as a third step. The product from Process 2 comprises 0.7% sodium alginate. The products were packaged in conventional snus pouches and benchmarked with a commercial tobacco free nicotine product, CP1, comprising a microcrystalline cellulose as a filling agent, but not including any sodium alginate as a matrix forming agent. The products made according to the invention and CP1 were studied for stability and nicotine release.

For testing the nicotine release capacity of compositions according to the invention, pouches with products were made as outlined above with Process 1 and Process 2 and compared with CP1. The products were orally tested by respondents, taken out after a defined time period and processed for remaining nicotine. A consumed pouch was chopped into a 100 ml glass bottle and exposed to ultrasound together with 5 ml with Milli-Q water for 5 minutes. Thereafter, 100 ml of 0.05M potassium hydroxide solution was added, and the sample is shaken and then exposed to ultrasound for 60 minutes. The sample is shaken overnight on a vibrating table and is exposed to ultrasound an additional 30 minutes on the day after. Thereafter the sample is centrifuged and diluted to the desired level, the internal standard was added, and the sample was then analyzed by LC/MS/MS. The averaged results of three tests are demonstrated in Table 4, below.

TABLE 4

| | Initial nicotine content (mg/g) | Nicotine content after 38 min (mg/g) | Release of nicotine (mg/g) |
|---|---|---|---|
| Product from Process 1 | 6.13 | 2.57 | 3.56 (26%) |
| Product from Process 2 | 6.43 | 3.52 | 2.91 (45%) |
| CP1 | 8.9 | 5.7 | 3.2 (36%) |

Table 4 demonstrates that the amount of matrix forming agent of the inventive compositions can be used to control the release rate of nicotine. The alternate methods of manufacturing the compositions can be used to control the amount of bound nicotine to the alginate of the matrix forming agent. The results of Table 8 demonstrate a higher amount of bound nicotine is obtained when nicotine is added together with the matrix forming agent as a third, final step in the manufacturing process.

Example 3

In order to further assesses the stabilizing effect of the antioxidant according to the invention, products with about 1% (wt) nicotine were made in accordance with the recipe of Table 2 and with process 1 according to Example 2. These products were made with and without an ammonium citrate antioxidant and compared with same commercial product (CP1) as 1 Example 2. For the stability tests, the products were all put in a heating cabinet at 40° C. and 75% humidity for 9 weeks (representing 7 months in room temperature). The results of tested losses of nicotine, pH and water content are presented in Tables 5-7 below.

TABLE 5

| | Initial Amount nicotine % (wt) | Amount nicotine after 9 weeks | % Nicotine loss |
|---|---|---|---|
| Product with antioxidant | 1 | 0.85 | 15 |
| Product without antioxidant | 1.1 | 0.81 | 26 |
| CP1 | 1 | 0.74 | 26 |

TABLE 6

| | Initial pH | pH after 9 weeks | % pH reduction |
|---|---|---|---|
| Product with antioxidant | 8.6 | 8.3 | 3 |
| Product without antioxidant | 8.9 | 8.3 | 7 |
| CP1 | 8.4 | 7.9 | 6 |

TABLE 7

| | Initial water content % (wt) | Water content % (wt) after 7 months | % change |
|---|---|---|---|
| Product with antioxidant | 41.2 | 42.7 | +4 |
| Product without antioxidant | 46.9 | 43.1 | −8 |
| CP1 | 41.9 | 39.8 | −5 |

The results of Table 5-7 demonstrate the stabilizing capacity of the inventive composition comprising an ammonium citrate antioxidant.

The invention claimed is:

1. A composition for use in the oral or nasal cavity, wherein the composition comprises an active agent selected from the group consisting of nicotine and a cannabinoid, a matrix forming agent comprising alginate and suitable salts thereof, a filling agent, a pH adjuster, and an antioxidant comprising an ammonium citrate wherein the antioxidant is an effective complex binder at a pH of 8 to 9, and the pH adjuster is to adjust the pH of the composition to a pH of 8 to 9, and is selected from the group consisting of monocarbonate, bicarbonate, sesquicarbonate, acetates, glycinates, gluconates, borates, glycerophosphates, citric acid, phosphates, sodium hydroxide, potassium hydroxide, and mixtures thereof.

2. The composition according to claim 1, wherein the matrix forming agent comprises an at least one additional pharmaceutically acceptable gum.

3. The composition according to claim 1, wherein the matrix forming agent comprises at least 50% (weight) of alginate and suitable salts thereof.

4. The composition according to claim 1, comprising 5 to 95% (wt) of filling agent, comprising at least one plant fiber.

5. The composition according to claim 4, wherein the filling agent further comprises a polyol.

6. The composition according to claim 1, comprising at least one excipient selected from the group consisting of preservatives, taste or flavour enhancers, plasticizers and sweeteners.

7. The composition according to claim 1, comprising less than 50% (wt) of the matrix forming agent.

8. The composition according to claim 1, adapted to delivery to the nasal cavity, comprising less than 20% (wt) water.

9. The composition according to claim 8, wherein the composition comprises powder particles having a particle size range of 0.01 to 2 mm.

10. The composition according to claim 8, wherein the filling agent comprises a water soluble cellulose.

11. The composition according to claim 1, adapted to contact with a mucous membrane of the oral cavity, comprising at least 30% (wt) of water and a filling agent comprising at least one member selected from the group consisting of microcrystalline cellulose and other plant fibers.

12. The composition according to claim 1, comprising 40 to 60% (wt) water.

13. The composition according to claim 1, adapted to contact with a mucous membrane of the oral cavity, comprising less than 40% (wt) of water and filling agent comprising at least one member selected from the group consisting of microcrystalline cellulose and other plant fibers.

14. The composition according to claim 1, configured as a film suitable for transmucosal delivery of active agent having a thickness 0.01 to 7 mm, comprising at least 50% (wt) of the matrix forming agent and optionally a plasticizer.

15. The composition according to claim 14, comprising 0.1 to 20% (wt) of filling agent and a plasticizer.

16. The composition according to claim 1, wherein the alginate is sodium alginate.

17. A method of manufacturing a composition according to claim 1, comprising:
   (i) dry mixing filling agent and at least one of the matrix forming agent, an antioxidant and optionally at least one taste or flavour enhancer;
   (ii) mixing the dry mixture with a first aqueous solution comprising a pH adjuster;
   (iii) adding a second aqueous solution comprising at least one of a preservative, a taste or flavour enhancer and a sweetener;
   (iv) adding a third aqueous solution comprising active agent and mixing all added components to a mixture with a suitable amount of water.

18. The method according to claim 17, wherein the filling agent is dry mixed with the matrix forming agent, the antioxidant and optionally at least one taste or flavour enhancer.

19. The method according to claim 17, comprising dry mixing the filling agent, the antioxidant and optionally at least one taste or flavour enhancer, and wherein the third aqueous solution comprises the matrix forming agent and active agent.

20. The method according to claim 17, configured to produce a powder composition for nasal use by one or more further processing steps of the resulting mixture, comprising drying to a powder of a particle size of less than 2 mm with less than 15% water (wt).

21. The method according to claim 17, configured to produce a composition for use in the oral cavity by one or more further processing method of the resulting mixture with at least one of filling in pouches, tablet or lozenge forming, extrusion, punching, casting, moulding, injection moulding, kneading spinning, film forming and admixing with chewing gum base.

\*  \*  \*  \*  \*